United States Patent [19]

Arnold et al.

[11] Patent Number: 5,324,649
[45] Date of Patent: Jun. 28, 1994

[54] ENZYME-CONTAINING GRANULES COATED WITH HYDROLYZED POLYVINYL ALCOHOL OR COPOLYMER THEREOF

[75] Inventors: Raymond E. Arnold, San Francisco; Nathaniel T. Becker, Burlingame; Matthew G. Boston, San Carlos, all of Calif.; Aino Mansikkamaki, Hanko, Finland; Curran M. Simpson, Montara; Daniel J. Wendt, Belmont, both of Calif.

[73] Assignee: Genencor International, Inc., Rochester, N.Y.

[21] Appl. No.: 957,973

[22] Filed: Oct. 7, 1992

Related U.S. Application Data

[63] Continuation-in-part of Ser. No. 772,510, Oct. 7, 1991, abandoned.

[51] Int. Cl.$^5$ .............. C12N 9/98; C12N 11/08; C11D 10/00; D06M 16/00
[52] U.S. Cl. .................. 435/187; 252/174.12; 252/DIG. 12; 435/175; 435/176; 435/177; 435/180; 435/182; 435/264
[58] Field of Search ............. 435/182, 180, 187, 175, 435/176, 177, 180, 182, 264; 252/174.12, DIG. 12

[56] References Cited

U.S. PATENT DOCUMENTS

| | | | |
|---|---|---|---|
| 3,798,128 | 3/1974 | Munato et al. | 195/68 |
| 4,009,076 | 2/1977 | Green et al. | 195/63 |
| 4,689,297 | 8/1987 | Good et al. | 435/174 |
| 4,707,287 | 11/1987 | Herdeman | 252/91 |
| 4,898,781 | 2/1990 | Onouchi et al. | 428/402.22 |

FOREIGN PATENT DOCUMENTS 61-162185  7/1986  Japan .

Primary Examiner—David M. Naff
Attorney, Agent, or Firm—Margaret A. Horn

[57] ABSTRACT

A granular enzyme composition is produced, having reduced tendencies to form dust and leave residue, and exhibiting improved stability and delayed release characteristics. The granular composition comprises a core, an enzyme layer and an outer coating layer. The enzyme layer, and optionally the core and outer coating layer, contain a vinyl polymer. The vinyl polymer is preferably a hydrolyzed polyvinyl alcohol or copolymer thereof. The hydrolyzed polyvinyl alcohol has varying degrees of hydrolysis in the core, enzyme layer and outer coating layer. Also disclosed are methods for making such enzyme-containing granules, the methods having greatly reduced processing time.

38 Claims, 4 Drawing Sheets

ENZYME-CONTAINING GRANULES COATED WITH HYDROLYZED POLYVINYL ALCOHOL OR COPOLYMER THEREOF

CROSS REFERENCE TO RELATED APPLICATIONS

This application is a continuation-in-part of U.S. application Ser. No. 07/772,510, filed Oct. 7, 1991, now abandoned.

FIELD OF THE INVENTION

This invention relates to improvements in or relating to enzyme granules, as well as improved processes for producing such granules.

BACKGROUND OF THE INVENTION

Recently the use of enzymes, especially of microbial origin, has been more and more common. Enzymes are used in several industries including, for example, the starch industry, the dairy industry, and the detergent industry. It is well known in the detergent industry that the use of enzymes, particularly proteolytic enzymes, has created industrial hygiene concerns for detergent factory workers, particularly due to the health risks associated with dustiness of the available enzymes.

Since the introduction of enzymes into the detergent business, many developments in the granulation and coating of enzymes to reduce enzyme dust have been offered by the industry. However, in today's state of ever-increasing environmental concern and heightened awareness of industrial hygiene, there remains a continuing need for low dust enzyme granules. Furthermore, there are additional characteristics desirable in enzyme granules not currently available in known granulation products. Some of these additional characteristics are related to the need to further alleviate industrial hygiene concerns (lower cost granules) while optimizing customer and end-user satisfaction (oxidatively stable and low residue granules) with the product while simultaneously reducing the cost of granulation (improved processing time), thus reducing cost of the overall enzyme product.

Principal among these desirable characteristics is the need for delayed release of the enzyme, preferably without having to increase the amount of chlorine scavenger additives currently used in granulation techniques. This delayed release has potential benefit, for example, in protecting enzymes from oxidation or autolytic degradation in washing machines until sufficient amounts of stabilizing proteins or peptides are released from dirty clothing into the wash water. Additional desirable characteristics include low residue granule formulations (where low residue is defined as a reduced tendency to leave noticeable undissolved residues on clothes or other material). This characteristic is desirable to the customer (end-user) of a detergent formulation. In addition, improved stability (enhanced shelf life) formulations are needed in the industry. Accomplishing all these desired characteristics simultaneously while maintaining cost containment for the granule production is a particularly challenging task. For example, many potential polymers to delay the release of the enzyme leave behind insoluble residues, which are undesirable to the user, or such polymers cause increased processing time, which causes increased costs. Also, most potential granulating cores which are attrition-resistant and, therefore, suitable for producing low dust granules, tend to leave behind insoluble residues.

Therefore, it is an object of the present invention to provide low dust, low residue, delayed release enzyme granules. These granules preferably have increased stability. It is another object of the present invention to provide processes and enzyme granule compositions which afford the formation of such improved granules in much lower processing time, thus reducing cost of the granular product.

SUMMARY OF THE INVENTION

According to the present invention, there are provided improved enzyme-containing granules such granules comprising:

a) a core comprising one or more water soluble or dispersible agent(s) which core material is characterized by leaving a low residue upon dispersion, said core being optionally coated with a vinyl polymer or vinyl copolymer;

b) an enzyme layer comprising one or more enzymes and a vinyl polymer or copolymer; and c) an outer coating comprising a vinyl polymer or copolymer and, optionally, a low residue pigment and/or a lubricant.

In a preferred embodiment of the enzyme granule of the present invention, the vinyl polymer useful in the core, enzyme and outer coating layers is a polyvinyl alcohol (PVA).

In a further preferred embodiment of the present invention, the core material is a nonpareil (sugar or salt) which has been coated with a PVA. In another embodiment of the present invention, the coating on the core may comprise additional agents such as a plasticizer.

The enzyme-containing granules of the present invention may comprise any enzyme; however, in a preferred embodiment of the present invention, the enzyme is selected from the group consisting of proteases, amylases, lipases, cellulases or mixtures thereof.

In a preferred embodiment of the present granule, the enzyme layer comprises a PVA either alone or in combination with additional agents such as plasticizers or anti-agglomeration agents.

In yet another embodiment of the present invention, a scavenger layer (chlorine scavenger) is present, preferably immediately outside of the enzyme layer.

The enzyme-containing granules of the present invention preferably comprise an outer coating of PVA or mixture of various PVAs. More preferably, the outer coating comprises an integral mixture of PVA, a low residue pigment and a lubricant.

This invention also comprises methods for making low dust granules. A method embodiment of the present invention comprises:

a) selecting a core material which is a water soluble or dispersible agent coated with a suitable vinyl polymer or copolymer;

b) coating the core of step a) with one or more enzymes and a suitable vinyl polymer or copolymer; and c) coating the product of step b) with a suitable vinyl polymer or copolymer, alone or in combination with a low residue pigment or a lubricant, or a mixture thereof.

In a preferred process embodiment of the present invention, the vinyl polymer used in step b) or c) of the process is a PVA or mixture of PVAs.

In a more preferred embodiment of the present invention, the method comprises selecting a core coated with PVA, and including PVA in the enzyme layer and in the outer coating layer. Most preferably, the outer coating layer further comprises a lubricant such as an ionic or nonionic surfactant.

DETAILED DESCRIPTION OF THE INVENTION

Figure 1:
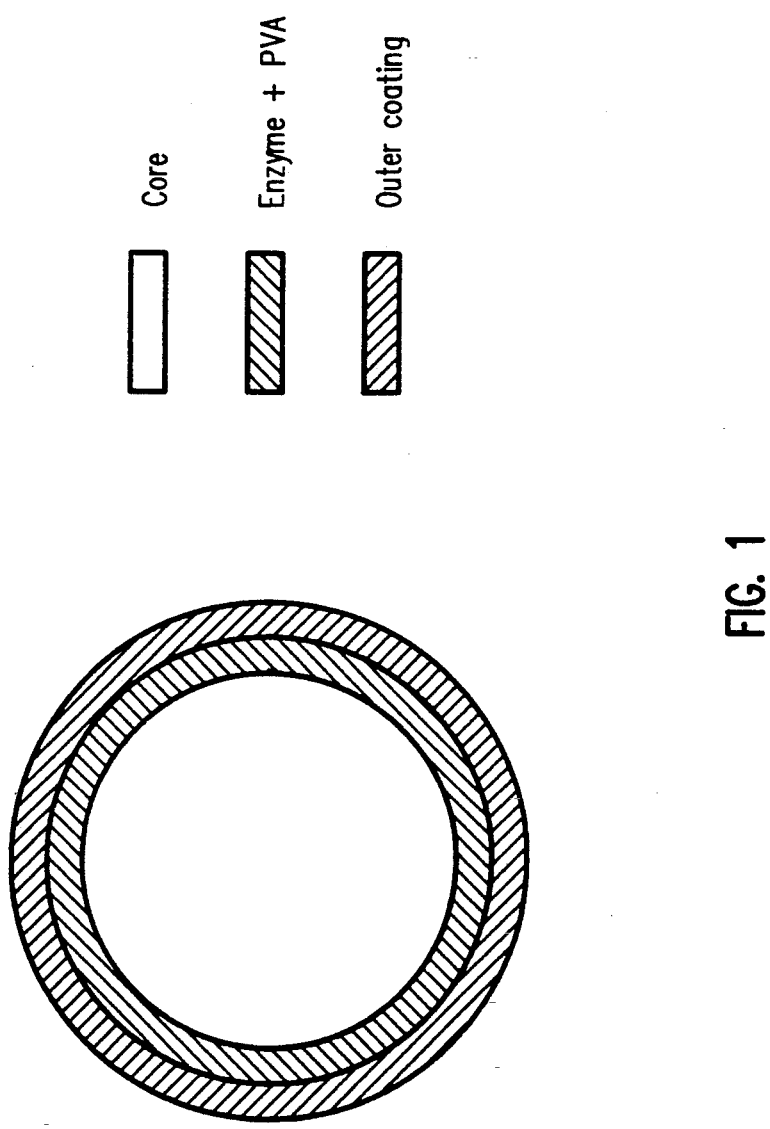
FIG. 1 is a cross-sectional diagram of an enzyme granule.
Figure 2:
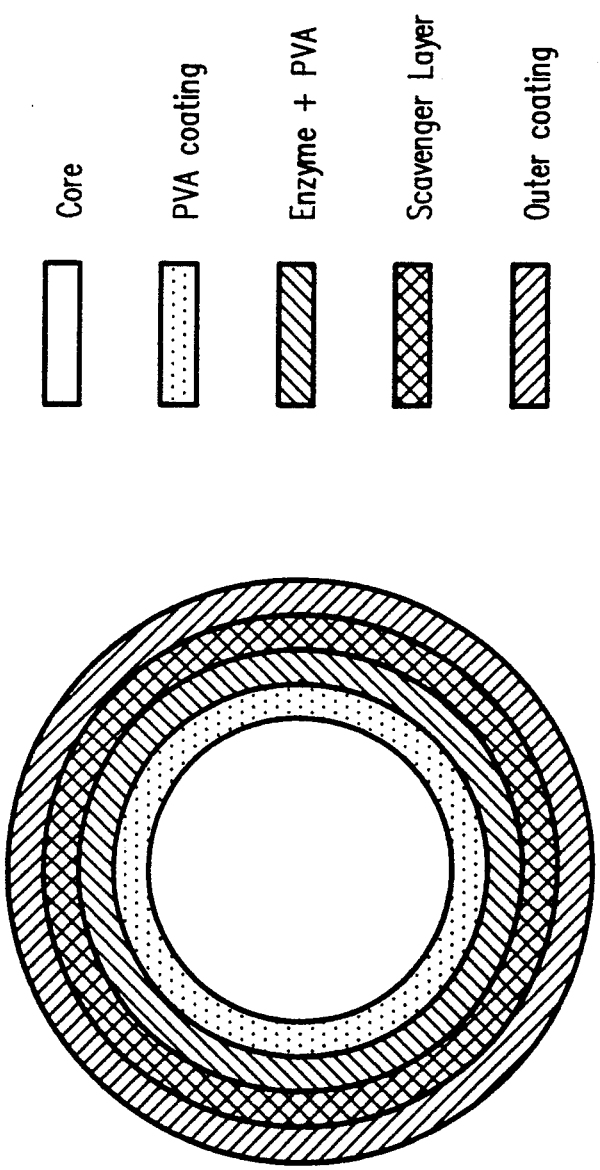
FIG. 2 is a cross-sectional diagram of an enzyme granule comprising additional layers.

Surprisingly, it has been found that the incorporation of a vinyl polymer or copolymer, and preferably polyvinyl alcohol, in one or more of the granule layers provides a granule having improved characteristics such as low dust, low residue (upon dissolution), delayed enzyme release and increased stability. It has also been found that such improved granules can be made in a much reduced processing time.

The preferred vinyl polymer useful in the present invention is polyvinyl alcohol (PVA), which is defined as a homopolymer or copolymer in which vinyl acetate is a starting monomer unit and in which most or all (70–100%) of the acetate moieties are subsequently hydrolyzed to alcohol moieties. Other vinyl polymers which may be useful in the present invention include, but are not limited to, polyvinyl acetate and polyvinyl pyrrolidone. Copolymers such as PVA-methylmethacrylate copolymer may also be used in the present invention. PVA is commercially available in a wide range of molecular weights, viscosities and varying degrees of hydrolysis from the polyvinyl acetate precursor. Table A sets forth the parameters for categorizing PVA based on these various characteristics.

TABLE A

| GRADES OF PVA COMMERCIALLY AVAILABLE | | |
|---|---|---|
| Degree Viscosity | Viscosity Centipose | Molecular Weight (MW) |
| ultra low | 3–5 | 5,000–25,000 |
| low | 5–15 | 25,000–50,000 |
| medium | 15–30 | 50,000–150,000 |
| high | 30–70 | 100,000–200,000 |
| Degree of Hydrolysis | | % Hydrolysis |
| partially | | 70–90 |
| intermediately | | 90–98 |
| fully | | 98–99 |
| super | | 99–100 |

Any of the PVAs listed in Table A may be used in the present invention.

The type of PVA used will depend in part on which layer of the granule the PVA is being used in, and will also depend on what characteristics of the granule are to be affected. For example, if PVA is used in the core, it is preferably partially hydrolyzed PVA and low viscosity (low molecular weight) because this will result in lower residue upon dissolution of the granule such as in a washing liquor. The PVA preferred for the enzyme layer is an intermediately, fully or super hydrolyzed PVA with low to medium viscosity. In addition, it is contemplated that mixtures of PVA may be used in any or all layers of the granules of the present invention.

Cores

The core particles suitable for use in the present invention are preferably of a highly hydratable material, i.e., a material which is readily dispersible or soluble in water. The core material should either disperse (fall apart by failure to maintain its integrity when hydrated) or solubilize by going into a true aqueous solution. Clays (bentonite, kaolin), nonpareils and agglomerated potato starch are considered dispersible. Nonpareils are spherical particles consisting of a seed crystal that has been built onto and rounded into a spherical shape by binding layers of powder and solute to the seed crystal in a rotating spherical container. Nonpareils are typically made from a combination of a sugar, such as sucrose, and a powder, such as corn starch. Alternate seed crystal materials include sodium chloride and other inorganic salts.

Particles composed of inorganic salts and/or sugars and/or small organic molecules may be used as the cores of the present invention. Suitable water soluble ingredients for incorporation into cores include: sodium chloride, ammonium sulfate, sodium sulfate, urea, citric acid, sucrose, lactose and the like. Water soluble ingredients can be combined with water dispersible ingredients. Cores can be fabricated by a variety of granulation techniques including: crystallization, precipitation, pan-coating, fluid-bed coating, rotary atomization, extrusion, spheronization and high-shear agglomeration.

The cores of the present invention may further comprise one or more of the following: fillers, plasticizers or fibrous materials. Suitable fillers useful in cores of the present invention include inert materials used to add bulk and reduce cost, or used for the purpose of adjusting the intended enzyme activity in the finished granulate. Examples of such fillers include, but are not limited to, water soluble agents such as urea, salts, sugars and water dispersible agents such as clays, talc, silicates, carboxymethyl cellulose or starches.

Suitable plasticizers useful in the cores of the present invention are nonvolatile solvents added to a polymer to reduce its glass transition temperature, thereby reducing brittleness and enhancing deformability. (The glass transition temperature, or Tg, represents the onset of segmental mobility for a polymer.) Typically, plasticizers are low molecular weight organic compounds and are highly specific to the polymer being plasticized. Examples include, but are not limited to, polyols (polyhydric alcohols, for example, alcohols with many hydroxyl radical groups such as glycerol, ethylene glycol, propylene glycol or polyethylene glycol), polar low molecular weight organic compounds such as urea, or other known plasticizers such as dibutyl or dimethyl phthalate, or water.

Suitable fibrous materials useful in the cores of the present invention include materials which have high tensile strength and which can be formed into fine filaments having a diameter of 1 to 50 microns and a length equal to at least four diameters. Typical fibrous materials include, but are not limited to: cellulose, glass fibers, metal fibers, rubber fibers, azlon (manufactured from naturally occurring proteins in corn, peanuts and milk) and synthetic polymer fibers. Synthetics include Rayon ®, Nylon ®, acrylic, polyester, olefin, Saran ®, Spandex ® and Vinal ®. Typical cellulose fibers would have an average fiber length of 160 microns with a diameter of about 30 microns.

In a granule embodiment of the present invention, the core is a water soluble or dispersible nonpareil, such as listed above, either coated by or built up from the seed crystal (nonpareil) using PVA either alone or in combination with anti-agglomeration agents such as titanium dioxide, talc, or plasticizers such as sucrose or polyols. The PVA may be partially hydrolyzed PVA, intermediately hydrolyzed PVA, fully hydrolyzed PVA (all as defined above), or a mixture thereof, with a low to high degree of viscosity. Preferably, the nonpareil is coated with partially hydrolyzed PVA, either alone or in combination with sucrose or such other plasticizer as known in the art. Partially hydrolyzed PVA is preferred because it results in a lower amount of residue upon dissolution of the granule than fully hydrolyzed PVA. The level of PVA in the coating of the nonpareil may represent from about 0.5% to 20% of the weight of the coated nonpareil. The core of the granules of the present invention, including any coating on such core material as described above, preferably comprises between about 40-85% by weight of the entire coated granule.

In a process embodiment of the present invention, the core material, which may be any material described herein, is charged into the granulator for coating with the first layer, i.e., the enzyme layer.

Enzymes

Any enzyme or combination of enzymes may be used in the present invention. Enzymes are typically coated from relatively impure solutions or slurries, in which the active enzyme constitutes only a portion of the total dissolved and suspended solids. Other suspended solids present in the fermentation broth include other proteins, peptides, carbohydrates, other organic molecules and salts. Preferred enzymes include those enzymes capable of hydrolyzing substrates, e.g., stains. These enzymes are known as hydrolases, which include, but are not limited to, proteases (bacterial, fungal, acid, neutral or alkaline), amylases (alpha or beta), lipases, cellulases, and mixtures thereof. Particularly preferred enzymes are subtilisins and cellulases. Most preferred are subtilisins such as described in U.S. Pat. No. 4,760,025 and U.S. Pat. No. 5,185,258 which are incorporated herein by reference, and cellulases or cellulase components isolated from *Trichoderma reesei* such as Cellulase 123 TM and Multifect TM L250, commercially available from Genencor International, or mixtures thereof or those described in commonly owned U.S. application Ser. No. 07/770,049 incorporated herein by reference.

The enzyme layer of the present invention contains, in addition to the enzyme per se, a vinyl polymer and preferably PVA. This polymer affects the release of the enzyme, delaying such release in a desirable fashion while not causing undesirable residue which is common with many delayed release agents. In a preferred embodiment of the present invention, the enzyme layer comprises intermediately, fully or super hydrolyzed PVA of low to medium viscosity. More preferably the PVA is fully hydrolyzed with a low degree of viscosity. Fully hydrolyzed PVA, at a level of about 0.25% to 3% of the granule weight, provides the desirable characteristic of delayed release of the enzyme to prevent immediate inactivation of the enzyme by residual wash water chlorine or to prevent inactivation by autolysis before the release of stain peptides into the wash.

It is surprising that fully hydrolyzed PVA, which has reduced water solubility and thus meets the delayed release criteria of the present invention, simultaneously contributes to reduction in the tendency of the granule to form dust and meets the low residue criterion of the present invention. This is apparently due to the low levels of fully hydrolyzed PVA used herein, which is an effective amount for delaying release, but a low enough level to prevent residue problems.

The enzyme layer may also further comprise plasticizers and anti-agglomeration agents. Suitable plasticizers useful in the present invention include polyols such as sugars, sugar alcohols or polyethylene glycols (PEGs) having a molecular weight less than 1,000, ureas or other known plasticizers such as dibutyl or dimethyl phthalate, or water. Suitable anti-agglomeration agents include fine insoluble material such as talc, $TiO_2$, clays and amorphous silica.

The enzyme layer of the present invention, including any nonenzyme solids and PVA therein, comprises between about 5%-70% by weight of the coated granule.

Coating Layers

The granules of the present invention may comprise one or more coating layers. For example, such coating layers may be one or more intermediate coating layers, or such coating layers may be one or more outside coating layers, or a combination thereof. Coating layers may serve any of a number of functions in a granule composition, depending on the end use of the enzyme granule. For example, coatings may render the enzyme resistant to oxidation by bleach, or coating layers may bring about the desirable rate of dissolution upon introduction of the granule into an aqueous medium, or provide a barrier against ambient moisture in order to enhance the storage stability of the enzyme and reduce the possibility of microbial growth within the granule.

In an embodiment of the present invention, the outer coating layer comprises a vinyl polymer or copolymer, preferably PVA, and optionally a low residue pigment or other excipients such as lubricants. Such excipients are known to those skilled in the art. Furthermore, coating agents may be used in conjunction with other active agents of the same or different categories.

Suitable PVAs for incorporation in the coating layer(s) of the granule include partially hydrolyzed, fully hydrolyzed and intermediately hydrolyzed PVAs having low to high degrees of viscosity. Preferably, the outer coating layer comprises partially hydrolyzed PVA having low viscosity. Other vinyl polymers which may h useful include polyvinyl acetate and polyvinyl pyrrolidone. Useful copolymers include, for example, PVA-methylmethacrylate copolymer.

The coating layers of the present invention may further comprise one or more of the following: plasticizers, pigments, lubricants such as surfactants or antistatic agents and, optionally, additional enzymes. Suitable plasticizers useful in the coating layers of the present invention are plasticizers including, for example, polyols such as sugars, sugar alcohols or polyethylene glycols (PEGs) having a molecular weight less than 1000, ureas or other known plasticizers such as dibutyl or dimethyl phthalate, or water. Suitable pigments useful in the coating layers of the present invention include, but are not limited to, finely divided whiteners such as titanium dioxide or calcium carbonate, or colored pigments, or a combination thereof. Preferably such pigments are low residue pigments upon dissolution.

As used herein "lubricants" mean any agent which reduces surface friction, lubricates the surface of the granule, decreases static electricity, or reduces friability of the granules. Lubricants can also play a related role in improving the coating process, by reducing the tackiness of binders in the coating. Thus, lubricants can serve as anti-agglomeration agents and wetting agents.

In a preferred embodiment of the present invention, from both a granule and processing perspective, the outer coating layer comprises a lubricant. The lubricant reduces attritional dust even further than a PVA coating alone, dramatically decreases processing time and also improves solubility of the granule. It is contemplated that the lubricant added to the outer coating may comprise or replace at least about 30% of the polymer or pigment used in the coating. In a more preferred embodiment, the lubricant is added to the granule as an integral mixture of pigment/polymer/lubricant. As used herein, "integral mixture" means a layer resulting from coating well mixed solutions of the components (pigment/polymer/lubricant) as opposed to the separate addition (layered addition) of each component. As used herein, "pigment" means low residue pigment, such as titanium dioxide, and "polymer" means a vinyl polymer or copolymer, as defined herein, and preferably PVA or a copolymer thereof.

Suitable lubricating agents include, but are not limited to, surfactants (ionic, nonionic or anionic), fatty acids, antistatic agents and antidust agents. Preferably the lubricant is a surfactant and most preferably is an alcohol-based surfactant such as a linear, primary alcohol of a 9 to 15 carbon atom chain length alkane or alkene or an ethoxylate or ethoxysulfate derivative thereof. Such surfactants are commercially available as the Neodol® product line from Shell International Petroleum Company. Other suitable lubricants include, but are not limited to, antistatic agents such as Static-Guard TM, Downey TM, Triton X100 or 120 and the like, antidust agents such as Teflon TM and the like, or other lubricants known to those skilled in the art.

The outer coating layer of the present invention preferably comprises between about 1–20% by weight of the coated granule.

Other Adjunct Ingredients

Adjunct ingredients may be added to the enzyme granules of the present invention. Adjunct ingredients may include: metallic salts, solubilizers, activators, antioxidants, dyes, inhibitors, binders, fragrances, enzyme protecting agents/scavengers such as ammonium sulfate, ammonium citrate, urea, guanidine hydrochloride, guanidine carbonate, guanidine sulfonate, thiourea dioxide, monethyanolamine, diethanolamine, triethanolamine, amino acids such as glycine, sodium glutamate and the like, proteins such as bovine serum albumin, casein and the like, etc., surfactants, including anionic surfactants, ampholytic surfactants, nonionic surfactants, cationic surfactants and long-chain fatty acid salts, builders, alkalis or inorganic electrolytes, bleaching agents, bluing agents and fluorescent dyes, and caking inhibitors. These surfactants are all described in commonly assigned PCT Application PCT/U.S. No. 92/00384, which is incorporated herein by reference.

A preferred embodiment of the present invention comprises a scavenger layer comprising a chlorine scavenger such as ammonium sulfate. This scavenger layer preferably comprises between about 5%–30% by weight of the coated enzyme granule. This scavenger layer is preferably located between the enzyme layer and the outer coating, although it may be present elsewhere in the granule.

The granules described herein may be made by methods known to those skilled in the art of enzyme granulation, including fluidized bed spray-coating, pan-coating and other techniques for building up a granule by adding consecutive layers on top of a starting core material.

The following examples are representative and not intended to be limiting. One skilled in the art could choose other enzymes, cores, particles, methods and coating agents based on the teachings herein.

EXAMPLE 1

A batch of PVA/sucrose coated nonpareils was produced by coating a PVA/sucrose solution onto a standard batch of nonpareils. 100 pounds of −25/+40 mesh sucrose/starch nonpareils were charged into a 200 lb capacity coating pan rotating at 45 rpm and heated to a bed temperature of 150° to 170° F. A coating solution was prepared by mixing 112 lbs of an 18% w/w solution of partially hydrolyzed PVA with low viscosity (Airvol 705S, commercially available from Air Products, Inc.) with 144 lbs of a 67% sucrose solution. A total of 38.4 lbs of this unheated mixture were pumped onto the uncoated nonpareils over a period of twelve hours, providing a coating composed of 2.6% w/w PVA and 12.4% w/w sucrose, on the basis of the final product weight. This material was screened to −20/+45 mesh, yielding 101 lbs of usable product and 15 lbs of scrap. A 20 minute Heubach attrition test on 13.5 mgs of coated nonpareil cores (prior to enzyme application) resulted in a total dust reading of 4.2 mg.

In a Glatt GPCG-5 fluidized bed spray-coater, 6,300 grams of PVA/sucrose coated nonpareil cores were charged and fluidized to a bed temperature of 44° C. 11.62 kg of protease ultrafiltration concentrate produced from *B. subtilis*, at a concentration of 5.27% w/w protease and 25.7% w/w total solids (such that protease represented 20.5% of total feed concentrate solids), were mixed with a 1.53 kg solution of a 10% w/w fully hydrolyzed PVA with low viscosity (Elvanol 90-50, commercially available from E. I. du Pont de Nemours and Co., Inc.), and 153 grams of amorphous silica (Zeothix 265, commercially available from J. M. Huber Corporation). The enzyme concentrate contained 0.25% sorbitol and 0.5% sodium benzoate as formulation chemicals. This enzyme/PVA mixture was then sprayed onto the fluidized cores at a starting rate of 40 g/min, ramping up to 110 g/min over a three hour period, resulting in a weight gain of 3.28 kg. The bed temperature was gradually reduced from 46° to 37° C., and the inlet temperature was held at about 57° to 60° C. over the course of the feed ramp. Atomization air pressure was held at 4.0 bar.

After enzyme application, 7.65 kg of a 40% w/w solution of ammonium sulfate was sprayed onto the granules, at similar conditions to enzyme application, but at an atomization pressure of 3.5 bar. This added another 3.05 kg to the weight of granules. The mass balance of the solids weight gain for these two steps was 99.8%. Finally, a protective coating solution was applied, made by suspending 765 grams of titanium dioxide in 1.147 kg water, then adding 5.10 kg of a 15% partially hydrolyzed PVA with low viscosity (Elvanol 51-05) stock solution, to provide 6.95 kg of a suspension with net 11% w/w PVA and 11% w/w TiO₂ concentrations. The coating suspension was sprayed onto the ammonium sulfate coated granule at rates of 50–80 g/min, an inlet temperature of 63° to 67° C., an outlet temperature of 45° to 49° C., and an atomization air pressure of 4.0 bar. The final product was harvested at 13.285 kg, representing a 78% mass balance for the final coating step, and an overall 89% mass balance for all spray-coating steps. In terms of percent weight gain, the enzyme layer represented a 52% weight gain over the starting core, and the combined three layers represented a 119% weight gain over the core. Product was screened through a 20 mesh screen to remove any agglomerates.

EXAMPLE 2

Two separate lots of an identical enzyme granule formulation were made in a Glatt Uniglatt laboratory fluidized bed spray-coater. Processes for the two lots were virtually identical, so only the second run is described. The starting material was made by charging 595 grams of −20/+50 mesh PVA coated nonpareils into the fluidized bed. These cores were coated by a process similar to that described in Example 1, except that the coating solution consisted of an 18% PVA solution (Airvol 705S) without any sucrose added, and the PVA solution was sprayed onto sucrose/starch nonpareils until the applied PVA coating represented 18% of the weight of the final coated nonpareil mass. (The 18% PVA-coated nonpareils registered 21.0 mg total dust in a Heubach attrition test prior to addition of enzyme.) A 436 gram sample of protease concentrate at a 54 g/kg enzyme concentration and 26.1% total solids concentration was mixed with 94 grams of a 10% PVA (Elvanol 90-50) solution. (Thus, the enzyme represented 20.7% of the total solids in the feed.) The mixture was spray-coated onto the fluidized cores at a rate of 7 g/min in the Uniglatt, with inlet and outlet temperatures of 55° C. and 45° C., respectively, and an atomization air pressure of 4.0 bar.

Once the enzyme was applied, 588 grams of a 40% ammonium sulfate solution and 539 grams of a suspension containing 11% PVA (Elvanol 51-05) and 11% TiO₂ were applied under similar process conditions, with coating rates of 17 g/min and 7 g/min, respectively. The final product weighed 1,023 grams, prior to sieving, a 90% yield on overall solids gain. This represents a net weight gain over the core weight of about 18% for the enzyme layer and about 72% overall. Product was sieved between 20 and 50 mesh screens to remove agglomerates and fines.

Example 1 and Lot 2 of Example 2 were subjected to several tests and compared with a comparable commercial product, Savinase 6.0T (available from Novo-Nordisk Industri A/S). In a Heubach attrition test, using a fill volume of about 17 cc in a 20 minute test time with an airflow rate of 20 liters per minute desiccated air, the following comparative dust levels were obtained:

|  | Total dust (mg) | Enzyme dust (μg) |
|---|---|---|
| Savinase | 5.7 | 24 |
| Example 1 | 0.6 | 7 |
| Example 2, Lot 2 | 0.6 | 4 |

In a test for potential residue left by enzyme granules after a standard wash cycle at 60° F., Savinase 6.0T left a fine white residue on the cloth, indicating the presence of some insolubles. Examples 1 and 2 left equivalent or lower levels of residue than Savinase 6.0T.

Figure 3:
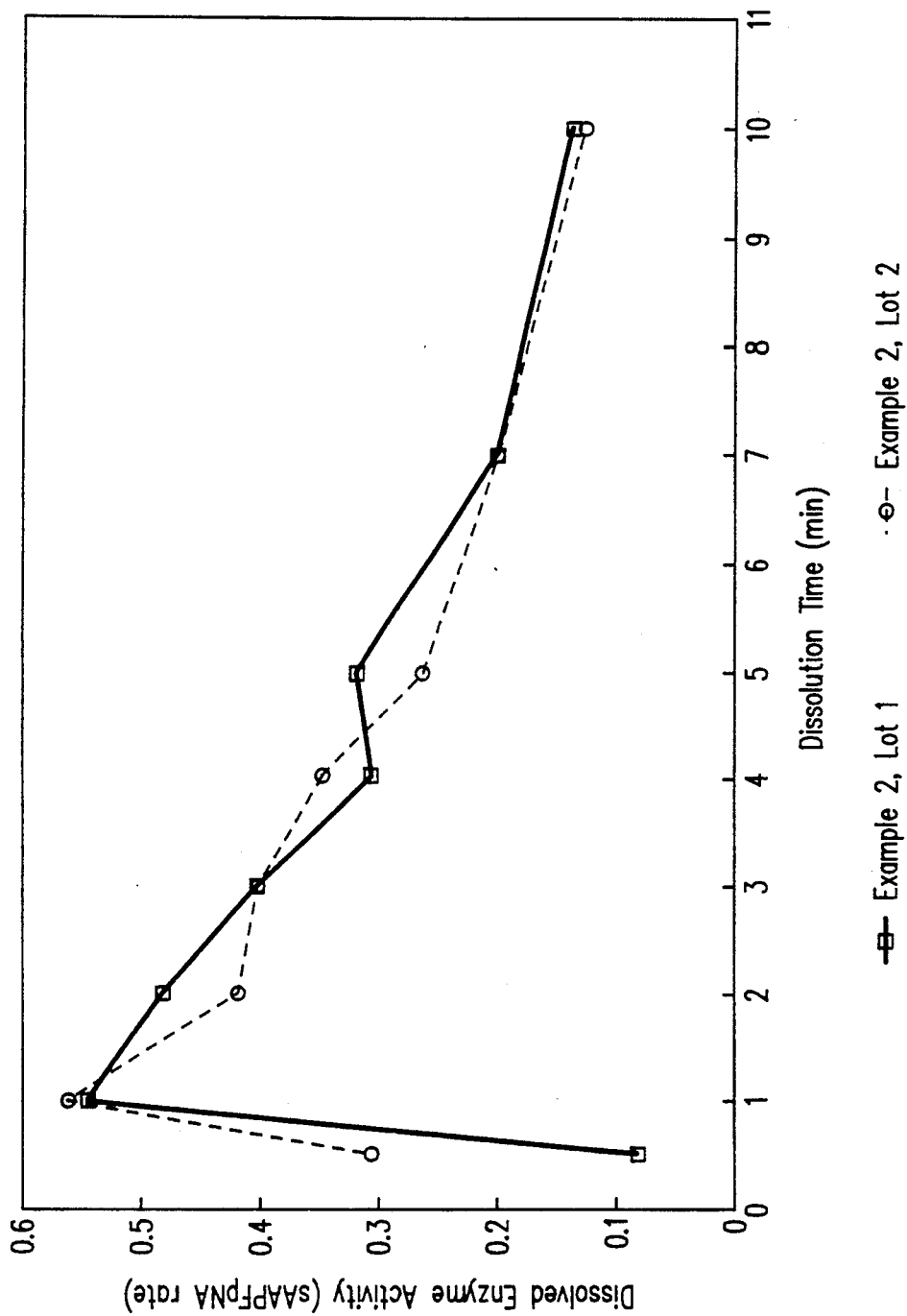
FIG. 3 is a graph showing dissolution profiles of certain enzyme granules.
Figure 4:
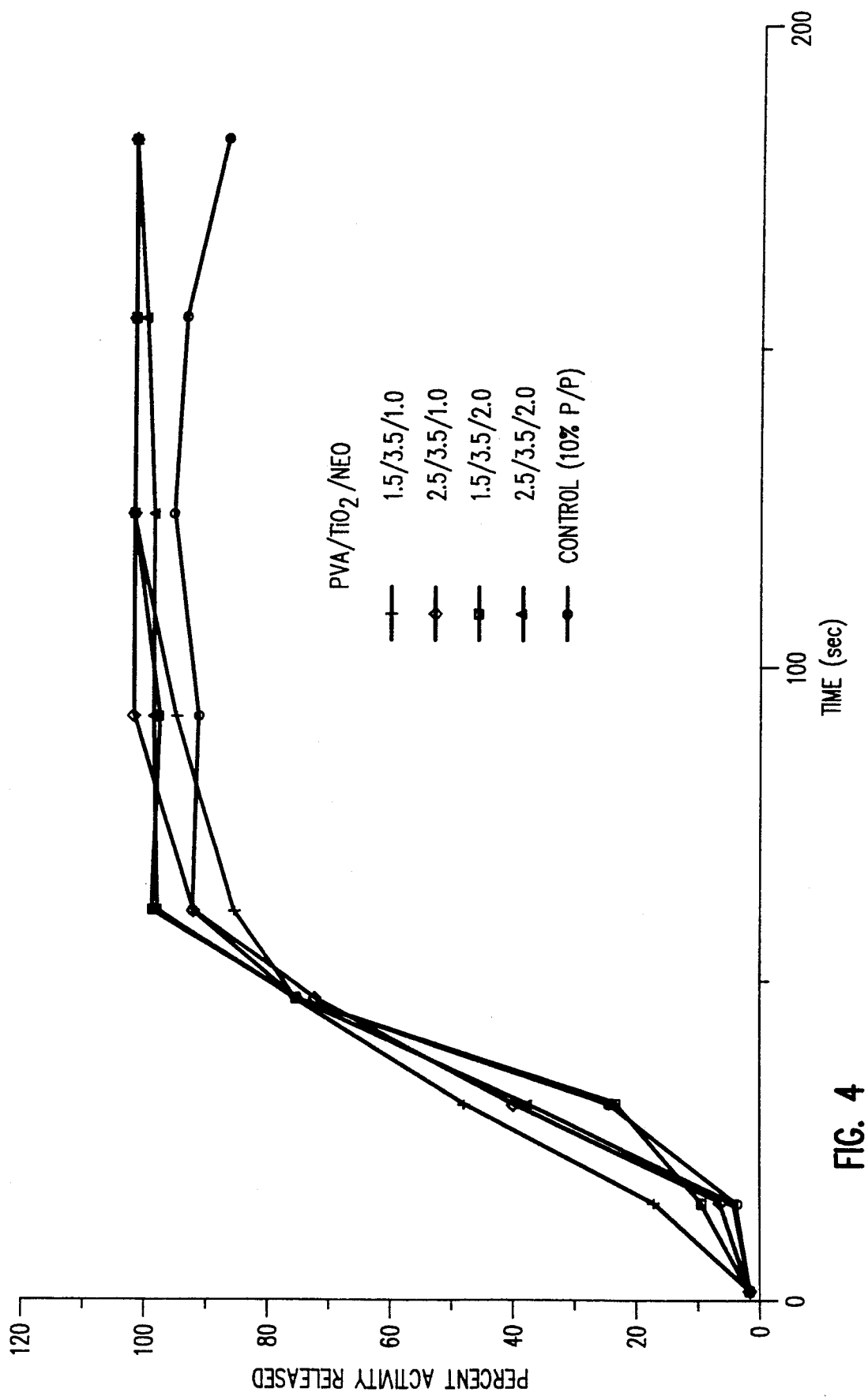
FIG. 4 shows dissolution profiles of enzyme granules comprising various ratios of polymer:pigment and polymer:pigment:lubricant.

Dissolution profiles indicating rates of enzyme release under realistic detergent conditions are shown in FIG. 3 for both lots of Example 2. These profiles were generated in a dissolution tester with detergent present at 120° F., 10 grains per gallon hardness and a fixed medium stir rate. Activities were measured using a synthetic substrate rate assay. Even at these high temperatures, it can be seen that the rate of enzyme release is delayed. This can be an advantage in that it allows time for scavenging of residue wash water chlorine by the ammonium sulfate in the granule and protein materials released from the clothing. The delay also protects the enzyme against high temperature autolysis until released proteins and peptides are available to inhibit autolysis via peptide inhibition.

EXAMPLE 3

A granulated cellulase for textile applications was produced in a Uniglatt spray-coater. 842 grams of −30/+50 mesh regular sucrose/starch nonpareils were charged into the coater and fluidized at a bed temperature of 42° to 48° C. A 321 gram solution of cellulase ultrafiltration concentrate from *T. reesei*, containing 6% w/w protein and 21% w/w total solids, was mixed with a 235 gram solution of 10% fully hydrolyzed PVA (Airvol 107). This mixture was sprayed onto the fluidized nonpareils at a rate of about 9 g/min, resulting in a weight gain of 88 grams, or about 10.5% w/w. Over the enzyme/PVA layer, 275 grams of a coating suspension containing 12.7% PVA (Airvol 205) and 12.7% TiO₂ was sprayed on, bringing the total granule weight to 1,000 grams, a total weight gain of 18.8%. Of the final granule, 6.0% w/w was cellulase protein.

In comparison with a competitive product, Denimax Acid T (commercially available from Novo-Nordisk Industri A/S), Example 3 had identical total Heubach dust, 25 mg in both cases. The polyvinyl alcohol binder and coating provided the granule of Example 3 with superior stability of the cellulase activity at high temperature and high humidity.

The cellulase granules produced in this example were evaluated for storage stability in comparison with a commercial product, Denimax Acid T (Novo-Nordisk Industri A/S). The amount of residual activity measured after storage for eight days at 37° C., at low and high relative humidity was as follows:

|  | Relative Humidity (R.H.) | |
|---|---|---|
|  | Residual Activity at 0% R.H. | Residual Activity at 60% R.H. |
| Example 3 | 117 | 112 |
| Denimax Acid T | 102 | 26 |

Thus, the use of polyvinyl alcohol in the enzyme layer, and especially in the outer coating, confers excellent protection against the destabilizing effects of high temperature in combination with high humidity.

EXAMPLE 4

A granulated detergent lipase was produced in the Uniglatt spray-coater. 456 grams of the PVA/sucrose coated nonpareils described in Example 1 were charged into the reactor. 1.882 liters of a lipase ultrafiltration concentrate containing 10 g/L enzyme and 16.5% w/w total solids was sprayed onto the cores without admixed PVA. Inlet and outlet temperatures averaged 60° and 45° C., respectively, allowing a coating rate of about 8 g/min at 4 bar atomization. A 432 gram suspension of 11% w/w PVA (Elvanol 51-05) and 11% w/w $TiO_2$ was sprayed onto the lipase coated cores. The lipase application added 307 grams to the cores, a 67% weight gain. The final product weight was 808 grams, prior to screening, a net 77% weight gain. A Heubach attrition test yielded a total dust level of 0.8 mg; no measurement of active lipase dust content was available.

EXAMPLE 5

A granulated detergent protease was produced in a Glatt fluidized bed spray-coater substantially as described in Examples 1 and 2; however, the outer coating formulation applied to the granulation product was an integral mixture of $TiO_2$/PVA/Neodol ® in quantities provided below:

|  | kg | Solution % | Dry Weight On Granule % |
|---|---|---|---|
| $TiO_2$ | 47.5 | 11.0 | 5 |
| PVA (51-05) | 38.0 | 8.8 | 4 |
| Neodol ® | 9.5 | 2.2 | 1 |
| Water | 337.0 | 78.0 | 0 |
|  | 432.0 | 100.0 |  |

The $TiO_2$/PVA/Neodol ® coating mixture, described above, was applied to 684 kg of uncoated product at a 10% level to yield 760 kg of final product. The coating was applied at a maximum spray rate of about 1.6 kg/min.

The overall coating time for application of this coating mixture was measured and compared to the overall coating time for previous examples (particularly Example 1) where a 50-50% mixture of PVA/$TiO_2$ and 0% Neodol ® were used. Such comparison showed that coating time was reduced by about 50% when a surfactant was incorporated in the coating mixture as compared to coating time for a pigment/polymer layer only.

The total dust for the product of Example 5 was 0.6 mg/13.5 g of product, as measured by the Heubach dust assay referred to in Example 2. Product wash performance and solubility were similar to Examples 1 and 2.

EXAMPLE 6

Following procedures substantially as described in Examples 1-3, three granulated cellulase and protease containing products were produced in a Uniglatt spray-coater.

The three experimental lots comprised the following compositions, coated on nonpareil core materials:

| Exp. # | Active Cellulase (%) | Active Protease (%) | Surfactant (wt %) | Pigm/Polym (wt %) |
|---|---|---|---|---|
| A | 6.5 | 0.56 | 4.49 | 3.67 |
| B | 6.5 | 0.52 | 0 | 3.14 |
| C | 6.5 | 0.59 | * | 6.11* |

*Surfactant suspended in polymer coating; therefore, total polymer and surfactant shown in Pigment/Polymer column In Experiment A, the non-enzyme coating comprised individual applications of pigment/polymer, $TiO_2$/PVA (Elvanol 51-05), and surfactant (Triton X120). Experiment B utilized no surfactant, only a pigment/polymer coating of $TiO_2$/PVA (Elvanol 51-05). In Experiment C, the non-enzyme coating comprised surfactant suspended in the polymer; thus, the coating in this experiment was Triton X120/Elvanol 51-05.

The three experimental lots (A, B and C) were tested for total dust level in the Heubach test referred to in Example 2. The following comparative dust levels were obtained:

| Exp # | Average dust (mg/13.5 g |
|---|---|
| A | 42.5 |
| B | 255.0 |
| C | 4.2 |

These results show that the distinct surfactant layer of Experiment A seems to lower dust; however, a more dramatic effect of lowering dust is evidenced when the surfactant is suspended in the PVA forming an integral mixture (see Experiment C).

In addition to lowering dust levels, it was observed that the addition of the surfactant as an integral mixture of the PVA coating layer, enhanced feed rate; thus, reducing the total processing time, as compared to feed rate for normal pigment/polymer coatings (without surfactant).

Granules made as described herein have improved dust characteristics when compared to other granules known in the art. These improved dust characteristics are achieved while other desirable characteristics of the granules, such as solubility, stability, delayed release and low residue, are maintained or improved. In addition, in certain embodiments of the present invention (i.e., Example 5), feed rate may be enhanced with resulting reduction in coating time without adversely affecting the desirable characteristics of the claimed granules. Thus, cost may be reduced while enhancing product characteristics.

What is claimed is:

1. An enzyme-containing granule comprising:
   a) a non-enzyme containing core comprising a water soluble or water dispersible material coated with polyvinyl alcohol or copolymer thereof hydrolyzed about 70-90%;
   an enzyme layer comprising a mixture of at least one enzyme and polyvinyl alcohol or copolymer thereof hydrolyzed about 98-99%; and
   c) an outer coating layer comprising polyvinyl alcohol or copolymer thereof hydrolyzed about 70-90%.

2. A granule of claim 1 wherein the copolymer in steps a), b) or c) is polyvinyl alcohol-methylmethacrylate copolymer.

3. A granule of claim 1 wherein the polyvinyl alcohol or copolymer thereof in a) has a low viscosity.

4. A granule of claim 1 wherein the core comprises a nonpareil.

5. A granule of claim 4 wherein the polyvinyl alcohol or copolymer thereof has a low viscosity.

6. A granule of claim 1 wherein the core further comprises a plasticizer.

7. A granule of claim 1 wherein the enzyme layer comprises at least one enzyme selected from the group consisting of protease, amylase, lipase and cellulase.

8. A granule of claim 7 wherein the enzyme is a protease.

9. A granule of claim 8 wherein the protease is a subtilisin.

10. A granule of claim 7 wherein the enzyme is a cellulase or a component thereof.

11. A granule of claim 7 wherein the enzyme is a lipase.

12. A granule of claim 7 wherein the enzyme is a protease and a cellulase.

13. A granule of claim 1 wherein the polyvinyl alcohol or copolymer thereof in b) has a low viscosity.

14. A granule of claim 1 wherein the enzyme layer further comprises:
 a) a plasticizer; or
 b) an anti-agglomeration agent.

15. A granule of claim 1 wherein the polyvinyl alcohol or copolymer thereof in c) has a low viscosity.

16. A granule of claim 1 wherein the outer coating layer c) further comprises a low residue pigment.

17. A granule of claim 16 wherein the pigment is titanium dioxide.

18. A granule of claim 1 wherein the outer coating layer c) further comprises a lubricant.

19. A granule of claim 18 wherein the lubricant is a nonionic or anionic surfactant.

20. A granule of claim 19 wherein the surfactant is a linear primary alcohol of a 9-15 carbon atom chain length alkane or alkene or an ethoxylate or ethoxysulfate derivative thereof.

21. A granule of claim 1 further comprising a scavenger layer.

22. A granule of claim 21 wherein the scavenger layer comprises ammonium sulfate.

23. An enzyme-containing granule comprising:
 a) a non-enzyme containing nonpareil core;
 b) an enzyme layer comprising at least one enzyme and polyvinyl alcohol hydrolyzed about 98-99% and having low viscosity; and
 c) an outer coating layer comprising polyvinyl alcohol hydrolyzed about 70-90% and having low viscosity.

24. A granule of claim 23 further comprising a low residue pigment in the outer coating.

25. A granule of claim 24 further comprising a lubricant in the outer coating.

26. A granule of claim 25 wherein the lubricant is a lubricant is a nonionic or ionic surfactant.

27. A granule of claim 26 wherein the surfactant is a linear primary alcohol of 9-15 carbon atom chain length alkane or alkene or an ethoxylate or ethoxysulfate derivative thereof.

28. A granule of claim 23 further comprising a scavenger layer.

29. An enzyme-containing granule comprising:
 a) a non-enzyme containing nonpareil core coated with polyvinyl alcohol hydrolyzed about 70-90% and having low viscosity;
 b) an enzyme layer comprising at least one enzyme and polyvinyl alcohol hydrolyzed about 98-99% and having low viscosity; and
 c) an outer coating layer comprising a polyvinyl alcohol hydrolyzed about 70-90% and having a low viscosity, a low residue pigment and a linear alkane or alkene primary alcohol of 9-15 carbon atom chain length, or an ethoxylate or ethoxysulfate derivative thereof.

30. A granule of claim 29 further comprising a scavenger layer.

31. A granule of claim 29 wherein the nonpareil core is further coated with a plasticizer.

32. A granule of claim 29 wherein the enzyme layer further comprises:
 a) a plasticizer; or
 b) an anti-agglomeration agent.

33. A granule of claim 29 wherein the enzyme layer comprises at least one enzyme selected from the group consisting of protease, amylase, lipase and cellulase.

34. A method for making an enzyme-containing granule, said method comprising:
 a) selecting a water soluble or dispersible core material;
 b) coating the core of step a) with an enzyme layer comprising a mixture of at least one enzyme and polyvinyl alcohol or copolymer thereof hydrolyzed about 98-99%; and
 c) coating the product of step b) with polyvinyl alcohol or copolymer thereof hydrolyzed about 70-90%; alone or in combination with one or more pigments or lubricants.

35. A method of claim 34 comprising:
 a) selecting as the core material a nonpareil core coated with polyvinyl alcohol hydrolyzed about 98-99% and having a low viscosity;
 b) coating the coated core of step a) with at least one enzyme and polyvinyl alcohol hydrolyzed about 98-99% and having a low viscosity; and
 c) coating the product of step b) with an integral mixture comprising:
  1) polyvinyl alcohol hydrolyzed about 70-90% and having a low viscosity;
  2) a low residue pigment; and
  3) a lubricant.

36. A method of claim 35 wherein the lubricant of step c) is a nonionic or ionic surfactant.

37. A method of claim 36 wherein the surfactant is a linear alkane or alkene primary alcohol of 9-15 carbon atom chain length, or an ethoxylate or ethoxysulfate derivative thereof.

38. A method of claim 34 further comprising coating the product of step b) with a suitable chlorine scavenger prior to applying the coating of step c).

* * * * *